(12) United States Patent
Mason et al.

(10) Patent No.: US 11,087,240 B2
(45) Date of Patent: Aug. 10, 2021

(54) ENABLING SECURE HANDOVER OF INFORMATION BETWEEN USERS (71) Applicant: KONINKLIJKE PHILIPS N.V., Eindhoven (NL)

(72) Inventors: Jonathan David Mason, Waalre (NL); Angelique Carin Johanna Maria Brosens-Kessels, Noord Brabant (NL); Jia Du, Waalre (NL); Paul Augustinus Peter Kaufholz, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 947 days.

(21) Appl. No.: 14/768,242

(22) PCT Filed: Mar. 12, 2014

(86) PCT No.: PCT/IB2014/059666
§ 371 (c)(1),
(2) Date: Aug. 17, 2015

(87) PCT Pub. No.: WO2014/147521
PCT Pub. Date: Sep. 25, 2014

(65) Prior Publication Data
US 2015/0379433 A1    Dec. 31, 2015

Related U.S. Application Data (60) Provisional application No. 61/803,838, filed on Mar. 21, 2013.

(51) Int. Cl.
*G06Q 10/00* (2012.01)
*G16H 40/20* (2018.01)
*G06Q 50/00* (2012.01)

(52) U.S. Cl.
CPC ............. *G06Q 10/00* (2013.01); *G06Q 50/00* (2013.01); *G16H 40/20* (2018.01)

(58) Field of Classification Search
CPC ........ G06Q 10/00; G06Q 30/00; G06Q 50/00; G16H 40/20; G06H 10/00; G06H 15/00; G06H 10/60; G06H 10/65
See application file for complete search history.

(56) References Cited

U.S. PATENT DOCUMENTS

| | | | | |
|---|---|---|---|---|
| 7,962,525 B2* | 6/2011 | Kansal | ............ | G06F 17/30038 707/706 |
| 8,214,242 B2* | 7/2012 | Agapi | .................. | G06Q 10/109 705/7.19 |
| 8,407,049 B2* | 3/2013 | Cromack | .......... | G06F 17/30743 704/235 |
| 9,058,635 B1* | 6/2015 | Rybkin | .................. | G06Q 50/24 |
| 2007/0188901 A1* | 8/2007 | Heckerman | ............ | G09B 19/00 360/23 |

(Continued)

OTHER PUBLICATIONS

Waibel, Advances in automatic meeting record creation and access, Apr. 22, 2008 (Year: 2008).*

(Continued)

*Primary Examiner* — Sangeeta Bahl (57) ABSTRACT

System (100) for enabling a secure handover of information between an outgoing user and an incoming user, the system comprising: an interface (120) for accessing handover data (122), the handover data being indicative of information to be communicated from the outgoing user (010) to the incoming user (020) during a handover event; and a monitoring subsystem (140) for i) receiving sensor data (042) from a sensor (040) monitoring the handover event, ii) based on the handover data, determining one or more attributes indicative of communication of the information, and iii) analyzing the sensor data in dependence on the one or more attributes to determine whether the information has been communicated to the incoming user during the handover event; a reporting subsystem (160) for reporting on a result of said determining.

12 Claims, 2 Drawing Sheets

(56) References Cited

U.S. PATENT DOCUMENTS

| | | | | |
|---|---|---|---|---|
| 2008/0033752 A1* | 2/2008 | Rodgers | ............... | G06F 19/00 705/2 |
| 2010/0198614 A1* | 8/2010 | Chopra | ............... | G16H 10/60 705/2 |
| 2011/0072362 A1* | 3/2011 | Denner | ............... | G06Q 10/109 715/751 |
| 2013/0294594 A1* | 11/2013 | Chervets | ............... | H04M 3/56 379/202.01 |
| 2014/0164510 A1* | 6/2014 | Abuelsaad | ............... | G06Q 10/109 709/204 |
| 2014/0278550 A1* | 9/2014 | Pestka | ............... | G06F 19/00 705/3 |

OTHER PUBLICATIONS

ACOG, Communication strategies for patient handoffs (Year: 2012).*

Wears, Improving handoffs in the emergency department (Year: 2009).*

Wong, M.C., PhD Thesis, "An exploration of shift-to-shift clinical handover and clinical handover improvement using a user-centred approach at the Royal Hobart Hospital, Tasmania, Australia", Nov. 2011, University of Tasmania.

Johnson, M. et al. "Developing a minimum dataset for electronic nursing handover". J Clin Nurs. Feb. 2012;21 (3-4):331-43. doi: 10.1111/j.1365-2702.2011.03891.x. Epub Nov. 15, 2011.

Brochure for Medical Handoff., www.e-handoff.com.

Strople, B. et al., "Can Technology Improve Intershift Report? What the Research Reveals." Journal of Provessional Nursing, vol. 22, No. 3 (May-Jun.), 2006, pp. 197-204.

Wong, M.C. et al., "A structured evidence-based literature review regarding the effectiveness of improvement interventions in clinical handover", Australian Commission on safety and Quality in Health Care, Apr. 2008, eHealth Services Research Group—ACSQHC Clinical Handover Literature Review.

Anderson, J. et al, "The Veterans affairs shift change physician-to-physician handoff project", The Joint Commission Journal on Quality and Patient Safety, Feb. 2010, vol. 36, No. 2.

* cited by examiner

ENABLING SECURE HANDOVER OF INFORMATION BETWEEN USERS

CROSS-REFERENCE TO PRIOR APPLICATIONS

This application is the U.S. National Phase application under 35 U.S.C. § 371 of International Application No. PCT/IB2014/059666, filed on Mar. 12, 2014, which claims the benefit of U.S. Provisional Application No. 61/803,838, filed on Mar. 21, 2013. These applications are hereby incorporated by reference herein.

FIELD OF THE INVENTION

The invention relates to a system and method for enabling a secure handover of information between an outgoing user and an incoming user.

The invention further relates to a computer program product comprising instructions for causing a processor system to perform said method.

BACKGROUND OF THE INVENTION

The handover of information between an outgoing user and an incoming user plays a role in various settings. Here, the term outgoing user refers to a user from which information needs to be transferred to another user, i.e., an incoming user. The incoming user may be a replacement for the outgoing user, for example as part of a shift change or a general transfer of responsibilities between said users. Such transfer of information between an outgoing user and an incoming user is also referred to as handover of information.

For example, in a hospital or similar environment, clinical information is typically communicated from staff on duty to a replacement staff at an end of a shift. Such clinical information may concern the state of patients, tasks to be completed in the next shift, etc. Other examples where such handover of information plays a role include control centers such as air traffic control and industrial environments such as power stations, oil rigs, etc.

It has been recognized that correct handover of information is of critical importance in preventing accidents. For example, if clinical information is wrongly communicated or not communicated at all during a clinical handover, the results can lead to serious risks for patients such as wrong drug prescription and administration and suboptimal treatment plans. Incorrect handover of clinical information may even lead to dangerous adverse events such as increased severity of a disease or death of the patient. A correct clinical handover is therefore important to the health and safety of patients.

There are many threats to such a correct handover of information. For example, when a shift ends, the replacement staff typically has to become aware of the issues and aspects that will require attention, action or monitoring during the next shift. However, whereas the replacement staff is typically alert and keen to start working, those who are about to leave may have been working a long shift and are therefore typically keen to leave as quickly as possible. This discrepancy may result in a slack clinical handover, which in turn may lead to clinical information being wrongly communicated or not communicated at all.

It is known to provide guidelines for conducting a clinical handover. It is thought that by adhering to such guidelines, a correct clinical handover is provided. For example, the National Health Service (NHS) in the UK has established such guidelines.

It is also known to use electronic tools for improving a clinical handover. A PhD thesis from M. C. Wong titled "*An exploration of shift-to-shift clinical handover and clinical handover improvement using a user-centred approach at the Royal Hobart Hospital, Tasmania, Australia*", November 2011, University of Tasmania, Australia, describes an electronic tool enabling a clinician to generate a clinical handover message for a particular patient by documenting the issues and background of the patient, highlighting the current actions requiring attention, providing a management plan for the patient and categorizing the patient in terms of urgency. It is said that the electronic tool may be used to support verbal handover in that it provides an additional mechanism for information transfer.

SUMMARY OF THE INVENTION

A problem of the electronic tool is that it insufficiently ensures a secure handover of information. Here, the adjective secure refers to a handover which is conducted such that the chance of miscommunication or absence of communication is reduced.

It would be advantageous to provide a system or method for enabling a more secure handover of information between an outgoing user and an incoming user.

To better address this concern, a first aspect of the invention provides a system for enabling a secure handover of information between an outgoing user and an incoming user, the system comprising:
  an interface for accessing handover data, the handover data being indicative of information to be communicated from the outgoing user to the incoming user during a handover event;
  a monitoring subsystem for i) receiving sensor data from a sensor monitoring the handover event, ii) based on the handover data, determining one or more attributes indicative of communication of the information, and iii) analyzing the sensor data in dependence on the one or more attributes to determine whether the information has been communicated to the incoming user during the handover event; and
  a reporting subsystem for reporting on a result of said determining.

In a further aspect of the invention, a method is provided for enabling a secure handover of information between an outgoing user and an incoming user, the method comprising:
  accessing handover data, the handover data being indicative of information to be communicated from the outgoing user to the incoming user during a handover event;
  receiving sensor data from a sensor monitoring the handover event;
  determining, based on the handover data, one or more attributes indicative of communication of the information;
  analyzing the sensor data in dependence on the one or more attributes to determine whether the information has been communicated to the incoming user during the handover event; and
  reporting on a result of said determining.

In a further aspect of the invention, a computer program product is provided comprising instructions for causing a processor system to perform the method set forth.

The aforementioned measures make it possible to conduct a secure handover of information between an outgoing user and an incoming user. For that purpose, an interface is provided for accessing handover data, e.g., on an internal or external storage device. The handover data is indicative of information that is to be communicated from the outgoing user to the incoming user during a handover event. The handover data is indicative of said information in that it may comprise the information, i.e., in a computer-readable form, or that it may indicate the information, e.g., by comprising a short reference to the information. The information is to be communicated during a handover event. The term handover event refers to a time at which the communication to the incoming user is to take place. For example, the handover event may be a handover meeting which includes the outgoing user and the incoming user as participants. In such a case, the handover data may be obtained in the form of handover presentation to be discussed during the clinical handover meeting.

Additionally, a monitoring subsystem is provided which receives sensor data from a sensor monitoring the handover event. The sensor monitors the handover event in that it senses and records certain aspects of the handover event, thereby generating sensor data. For that purpose, the sensor may be physically located at the handover event. The monitoring subsystem receives the sensor data from the sensor and thus obtains a recording of said aspects of the handover event. The monitoring subsystem analyzes the sensor data to determine whether the information has been communicated to the incoming user during the handover event. For that purpose, the monitoring subsystem makes use of the handover data to obtain one or more distinguishing aspects of the communication of the information, i.e., one or more attributes. The one or more attributes enable the monitoring subsystem to analyze the sensor data for specific indications and/or specific evidence that the communication has been communicated, e.g., by searching for the attributes, finding similar attributes, etc. As such, the monitoring subsystem can estimate whether the information has been communicated to the incoming user during the handover event. The result is then reported by a reporting subsystem, e.g., in the form of discrete Yes/No or a probability that the information is deemed to have been communicated to the incoming user.

The above measures have the effect the system is enabled to determine whether information has been communicated to the incoming user during the handover event since the system is provided with both an indication of the information by means of the handover data as well as recorded aspects of the handover meeting by means of the sensor data. The monitoring subsystem can thus analyze the recorded aspects of the handover event for specific indications and/or specific evidence that the information has been communicated to the incoming user during the handover event. The monitoring unit is therefore enabled to determine whether the information has been communicated to the incoming user. The result of this determining is then reported and thus made explicit, e.g., in the form of a Yes/No indication, a probability, etc. This enables a more secure handover in that the reporting can be used as verification whether the handover of the information went correctly, as feedback during the current handover, as feedback to improve future handovers, etc. Accordingly, the chances of miscommunication or absence of communication are reduced.

Optionally, the sensor data comprises a recording of communication during the handover event, and the monitoring subsystem is arranged for analyzing the sensor data by searching the recording. The sensor data thus provides a recording of the communication between participants at the handover event. Such communication between the participants may take various forms, including verbal communication as well as non-verbal communication such as written communication or visual cues. The monitoring subsystem analyzes the sensor data by searching the recording of the communication between the participants to determine whether the information to be communicated at the handover event was indeed communicated. Advantageously, by making use of a recording of the communication during the handover event, it can be more reliably determined whether the information has been communicated to the incoming user during the handover event. Advantageously, it is not needed to rely on other indirect indications or evidence.

Optionally, the one or more attributes comprise one or more keywords indicative of the information to be communicated, and the monitoring subsystem is arranged for analyzing the sensor data by searching the recording for the one or more keywords. The monitoring subsystem thus obtains one or more keywords based on the handover data which are indicative of the information to be communicated. This allows the system to efficiently determine that the information has been communicated to the incoming user during the handover event if the recording comprises the one or more keywords, e.g., as part of verbal or non-verbal such as written communication between the participants of the handover meeting.

Optionally, the sensor data comprises an audio recording of the handover event, and the monitoring subsystem is arranged for applying a speech recognition technique to the audio recording. The information is most likely to be communicated verbally during a handover event as verbal communication is a typically a principal form of communication during such a handover event. Accordingly, the system is enabled to analyze such verbal communication so as to determine whether the information has been communicated to the incoming user as part of the communication between participants of the handover event.

Optionally, the monitoring subsystem is arranged for analyzing the sensor data to determine a presence of the incoming user during the handover event. An absence of the incoming user during the handover event is a clear indication that the information was not communicated to the incoming user during the handover event. The monitoring subsystem analyzes the sensor data to determine the presence of the incoming user during the handover event, e.g., by searching for indications or evidence of the incoming user's presence and/or absence. Advantageously, the system can more reliably determine when the information has not been communicated to the incoming user during the handover event.

Optionally, the monitoring subsystem is arranged for determining the presence of the incoming user by applying a biometric identification technique to the sensor data to identify the incoming user. Biometric identification techniques are well suited to identify users such as the incoming user and thus to determine his/her presence during the handover event. For example, if the sensor data comprises an audio recording of the handover event, voice fingerprinting may be used to identify the incoming user in the audio recording. Another example is that if the sensor data comprises a video recording of the handover event, facial recognition may be used to identify the incoming user in the video recording.

Optionally, the reporting subsystem is arranged for assigning a task to the incoming user as identified, the task being based on the information that has been communicated to the incoming user. The recipient in the communication of the information is likely to be responsible for, and thus tasked with, further dealing with the information. Having identified who is the recipient in the communication of the information, i.e., who is the incoming user, the reporting subsystem automatically assigns a task to said incoming user, e.g., in a task list. Accordingly, it is not needed to manually assign such a task.

Optionally, the sensor data comprises a video recording of the handover event, and the monitoring subsystem is arranged for analyzing the video recording to determine a level of attention of the incoming user. An answer to the question whether the information has been communicated to the incoming user during the handover event depends at least in part on the capability of the incoming user to receive said information, i.e., to absorb and/or assimilate the information being communicated to him/her. The attention that the incoming user is paying is indicative of said capability. The monitoring subsystem analyzes the video recording of the handover event to estimate said level of attention, e.g., using eye-tracking or other techniques known per se from the field of video analysis. Accordingly, the system is enabled to take such attention of the incoming user into account in determining whether the information has been communicated to the incoming user during the handover event.

Optionally, the monitoring subsystem is arranged for analyzing the sensor data in real-time during the handover event, and the reporting subsystem is arranged for issuing a warning if the information is deemed not to have been communicated at an end of the handover event. By providing a warning if the information is deemed not to have been communicated at an end of the handover event, it is avoided that information which was, based on the handover data, expected to be communicated to the incoming user during the handover event is erroneously communicated or not communicated at all.

Optionally, the system further comprises a presentation subsystem for presenting the handover data during the handover event. Here, the handover data may serve multiple purposes, namely for being presented during the handover event as well as enabling the monitoring subsystem to determine whether the information has been communicated to the incoming user during the handover event. Advantageously, it is not needed to separately provide the system with handover data for the purpose of said determining. Rather, the system may make use of handover data provided primarily for the purpose of being presenting during the handover event, e.g., a handover presentation or handover task list.

Optionally, the handover event is a handover meeting scheduled for at least the outgoing user and the incoming user, and the reporting subsystem is arranged for analyzing the handover data to establish at least one of the group of: an agenda and a task list, for the handover meeting. Since the handover data is indicative of information to be communicated from the outgoing user to the incoming user during a handover meeting, it is typically also indicative of a time needed to communicate the information, e.g., based on a quantity or complexity of the information. Advantageously, the reporting subsystem automatically establishes an agenda for the handover meeting based on an analysis of the handover data. The handover data is also typically indicative of tasks associated with the communication of information during the handover meeting. Advantageously, the reporting subsystem automatically establishes a task list for use during the handover meeting.

Optionally, the handover event is a clinical handover event, the outgoing user and the incoming user are clinical users, and the information to be communicated is clinical information. The system is well suited for enabling a secure handover of clinical information.

Optionally, the handover data is constituted by one or more of the group of: a note from one of the clinical users, an agenda of one of the clinical users, an electronic patient record, patient data from a patient monitor and a clinical handover presentation. The handover data is thus constituted by one or more information elements which are typically already available for other purposes. The system may automatically retrieve such information elements, thereby establishing the handover data. Advantageously, it is not needed to manually generate handover data specifically for the purpose of enabling the system to determine whether the information has been communicated to the incoming user during the handover event. Rather, the system may automatically retrieve such handover data.

Optionally, the interface is arranged for obtaining the handover data from a hospital information system. The system is thus connected to a hospital information system via the interface, thereby providing the system with access to various information elements available within the hospital information system. Advantageously, the system can automatically obtain the handover data without a need to manually provide said data.

It will be appreciated by those skilled in the art that two or more of the above-mentioned embodiments, implementations, and/or optional aspects of the invention may be combined in any way deemed useful.

Modifications and variations of the method, and/or the computer program product, which correspond to the described modifications and variations of the system, can be carried out by a person skilled in the art on the basis of the present description.

The invention is defined in the independent claims. Advantageous yet optional embodiments are defined in the dependent claims.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Figure 1:
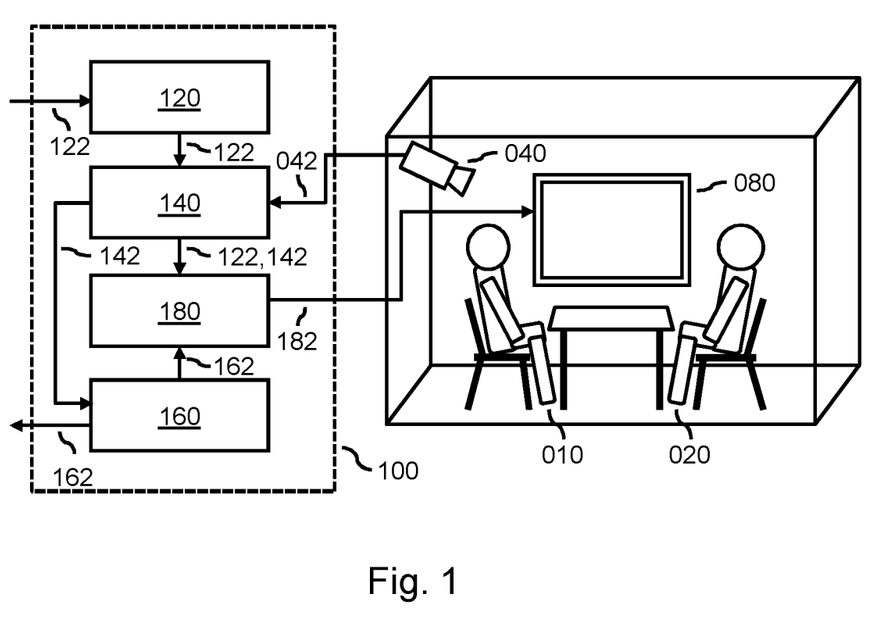
FIG. 1 shows a room in which an outgoing user and an incoming user are involved in a handover of information, as well as a system for enabling the secure handover of the information between the outgoing user and the incoming user.

FIG. 1 shows a system 100 for enabling a secure handover of information between an outgoing user and an incoming user. The system comprises an interface 120 for accessing handover data 122. In FIG. 1, the handover data 122 is shown to be accessed externally, i.e., from outside of the system 100. Alternatively, the interface 120 may access the handover data 122 internally, i.e., within the system 100. The handover data 122 accessed by the interface 120 is at least indicative of information to be communicated from the outgoing user to the incoming user during a handover event. The system 100 further comprises a monitoring subsystem 140 for receiving sensor data 042 from a sensor 040 monitoring the handover event. FIG. 1 shows the sensor 040 being provided in the form of a video camera 040 arranged in a room. The room is shown to be used by the outgoing user 010 and the incoming user 020 for a handover event, e.g., a handover meeting. FIG. 1 further shows the monitoring subsystem 140 receiving the sensor data 042 directly from the sensor 040. Alternatively, the sensor data 042 may be received from the sensor 040 via a storage device, i.e., by being temporarily stored after being recorded by the sensor 040.

The monitoring subsystem 140 is arranged for analyzing the sensor data 042 to determine whether the information has been communicated to the incoming user 020 during the handover event. For that purpose, the monitoring subsystem 140 is shown to receive the handover data 122 from the interface 120 so as to provide the monitoring subsystem 140 with at least an indication of the information to be communicated to the incoming user 020 during the handover event. The system 100 further comprises a reporting subsystem 160 for reporting on a result of said determining. For that purpose, the reporting subsystem 160 is shown to receive monitoring data 142 from the monitoring subsystem 140 which communicates said result to the reporting subsystem 160. Moreover, the reporting subsystem 160 is shown to provide reporting data 162 which establishes the reporting of the result. For example, the reporting data 162 may directly comprise the result as provided by the monitoring data 142. Alternatively, the reporting data 162 may comprise a different representation of the result, e.g., in the form of a report, document, log file, etc.

An operation of the system 100 may be briefly explained as follows. The interface 120 accesses the handover data 122. The monitoring subsystem 140 receives sensor data 042 directly or indirectly from the sensor 040. The monitoring subsystem 140 uses the handover data 122 determine one or more attributes indicative of communication of the information. The monitoring subsystem 140 subsequently analyzes the sensor data 042 in dependence on the one or more attributes to determine whether the information has been communicated to the incoming user during the handover event. The monitoring subsystem 140 provides a result of said determining to the reporting subsystem 160. The reporting subsystem 160 subsequently reports on the result of said determining.

The operation of the system 100 may be in real-time in that the sensor data 042 may be received during an ongoing handover event and may be analyzed in real-time during the handover event. Alternatively, the sensor data 042 may be received after a handover event and may be analyzed in real-time or non-real-time after the handover event.

Figure 2:
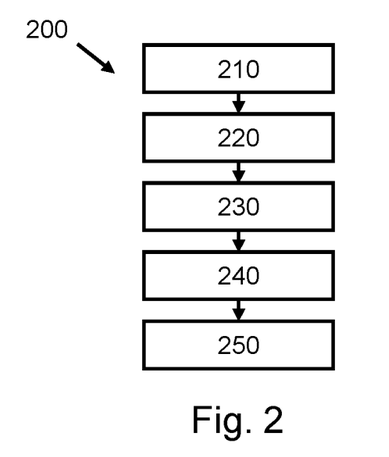
FIG. 2 shows a method for enabling the secure handover of information.

FIG. 2 shows a method for enabling a secure handover of information between an outgoing user and an incoming user. The method 200 may correspond to an operation of the system 100. However, the method 200 may also be performed in separation of the system 100, e.g., using a different system or device. The method 200 comprises, in a first step titled "ACCESSING HANDOVER DATA", accessing 210 handover data, the handover data being indicative of information to be communicated from the outgoing user to the incoming user during a handover event. The method 200 further comprises, in a second step titled "RECEIVING SENSOR DATA", receiving 220 sensor data from a sensor monitoring the handover event. The method 200 further comprises, in a third step titled "DETERMINING ATTRIBUTE(S)", determining 230, based on the handover data, one or more attributes indicative of communication of the information. The method 200 further comprises, in a fourth step titled "ANALYZING SENSOR DATA", analyzing 240 the sensor data in dependence on the one or more attributes to determine whether the information has been communicated to the incoming user during the handover event. The method 200 further comprises, in a fifth step titled "REPORTING RESULT", reporting 250 on a result of said determining. It is noted that the above steps may be performed in any suitable order. For example, the first and second steps may be performed simultaneously or in reverse order.

Figure 3:
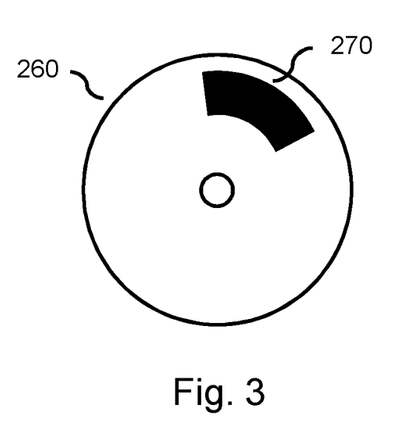
FIG. 3 shows a computer program product for performing the method.

FIG. 3 shows a computer program product 270 comprising instructions for causing a processor system to perform the aforementioned method 200. The computer program product 270 may be comprised on a computer readable medium 260, for example in the form of as a series of machine readable physical marks and/or as a series of elements having different electrical, e.g., magnetic, or optical properties or values.

The system 100 and the method 200 may be explained in more detail as follows. Here, reference is made to the aforementioned FIG. 1 as well as to FIGS. 4 and 5.

The monitoring subsystem 140 analyzes the sensor data 042 to determine whether the information has been communicated to the incoming user 020 during the handover event. For that purpose, the monitoring subsystem 140 may employ different techniques as well as different combinations of techniques. A first technique may be to analyze the sensor data 042 to determine a presence of the incoming user 020 during the handover event. A lack of presence, i.e., an absence, of the incoming user 020 may enable the monitoring subsystem 140 to directly determine that the information has not been communicated to the incoming user 020 during the handover event. It may therefore not be needed to consider the result of other techniques to determine whether the information has been communicated to the incoming user 020 during the handover event.

The monitoring subsystem 140 may determine the presence of the incoming user 020 by applying a biometric identification technique to the sensor data 042 to identify the incoming user 020. Depending on the type of sensor 040 and thus the type of sensor data 042, different biometric identification techniques may be employed. For example, if the sensor data 042 comprises an audio recording of the handover event, e.g., by the sensor 040 comprising a microphone, the monitoring subsystem 140 may use a voice fingerprinting technique to identify whether the incoming user 020 is present during the handover event. For that purpose, the handover data 122 may indicate the incoming user 020 to the monitoring subsystem 140 to enable the monitoring subsystem 140 to obtain a personal attribute of the incoming user 020, e.g., a reference voice fingerprint of the incoming user from an internal or external database. The monitoring subsystem 140 may then compare voice fingerprints from actual users present during the handover event to the reference voice fingerprint to determine whether the incoming user 020 to whom the information should be communicated was present during the handover event. Another example is the use of a facial recognition technique if the sensor data 042 comprises a video recording of the handover event. Facial recognition and voice fingerprinting may also be combined. Also other biometric identification techniques may be used, as are known per se from the field of biometric identification. Additionally or alternatively, non-biometric identification techniques may be used. For example, the sensor data 042 may comprise location data of the incoming user 020, e.g., as obtained by tracking the incoming user's mobile phone, which may be compared to a location of the handover event to determine his/her presence.

In this respect, it is noted that, in general, the sensor 040 may be a sensor subsystem in that it may comprise multiple individual sensor units. For example, the sensor 040 may be a video camera which comprises a light sensitive array as well as a microphone. Accordingly, the sensor data 042 may be comprised of different types of recorded data.

Another technique which may be employed by the monitoring subsystem 140 to determine whether the information has been communicated to the incoming user during the handover event is the following. The sensor data 042 may comprise a recording of communication between participants during the handover event. For example, the sensor data 042 may comprise an audio recording or a video recording of the handover event. The monitoring subsystem 140 may be arranged for analyzing such sensor data 042 by searching the communication for communication of the information. In particular, the monitoring subsystem 140 may determine one or more attributes based on the handover data such as one or more keywords which are indicative of communication of the information. The monitoring subsystem 140 may then search the recording of the communication for the one or more keywords. For example, if the sensor data 042 comprises an audio recording of the handover event, the monitoring subsystem 140 may be arranged for applying a speech recognition technique to the audio recording to obtain a transcript of the communication, and subsequently search the transcript for the one or more keywords. Another example is when the sensor data 042 comprises a video recording of the handover event. Here, the monitoring subsystem 140 may be arranged for recognizing written communication, e.g., as written on a whiteboard by participants of the handover event, and subsequently search the written communication for the one or more attributes, e.g., the one or more keywords.

The communication may also take different forms, e.g., a nodding of the incoming user 020, eye contact between the outgoing user 010 and the incoming user 020, etc. The sensor data 042 may also comprise recordings of such forms of communication, e.g., in the form of the aforementioned video recording. The monitoring subsystem 140 may analyze such forms of communication to determine whether the information was communicated to the incoming user 020. For that purpose, the monitoring subsystem 140 may determine one or more attributes based on the handover data which are specifically indicative of communication of the information in such forms of communication.

Another technique which may be employed by the monitoring subsystem 140 to determine whether the information has been communicated to the incoming user 020 during the handover event is the following. The sensor data 042 may comprise a video recording of the handover event, and the monitoring subsystem 140 may be arranged for analyzing the video recording to determine a level of attention of the incoming user 020. For that purpose, techniques such as eye-tracking may be used, as are known per se from the field of video analysis. Having determined the level of attention of the incoming user 020, the monitoring subsystem 140 may determine that the information has not been communicated to the incoming user 020 if the level of attention of the incoming user 020 is relatively low. In particular, the monitoring subsystem 140 may determine the level of attention of the incoming user 020 at a time when the outgoing user 010 attempts to communicate the information to the incoming user 020 in order to determine whether the information has been successfully communicated from the outgoing user 010 to the incoming user 020.

It will be appreciated that the present invention is not limited to the aforementioned techniques for analyzing the sensor data to determine whether the information has been communicated to the incoming user during the handover event. Other techniques as known per se from the fields of, e.g., natural language processing and computer vision may also be advantageously applied. In particular, machine learning may be used to implement or optimize such techniques. The attributes may be automatically determined as part of such machine learning. Moreover, interference engines such as reasoning engines may be used to obtain conclusions from the output of the above techniques.

The system 100 may or may not be aware of an identity of the incoming user at a time when receiving the sensor data 042. For example, the handover data 122 may only indicate the information to be communicated during the handover event, without identifying the incoming user 020. In such a case, the monitoring subsystem 140 may be arranged for identifying the incoming user 020 by determining who is the recipient of the information during the handover event. For example, the monitoring subsystem 140 may analyze a transcript of an audio recording of the handover event to determine when the information is communicated and subsequently identify a recipient of the information, e.g., by obtaining a voice fingerprint of a user who verbally acknowledges receipt of the information. The reporting subsystem 160 may report on the identity of the incoming user 020 as identified by the monitoring subsystem 140. The reporting subsystem 160 may report on said identity in association with the information that was communicated. In particular, the reporting subsystem 160 may assign a task to the incoming user 020, the task being based on the information that has been communicated to the incoming user. The task may relate to an action to be performed in association with the information that was communicated. For example, when the information concerns a low blood pressure of a patient, the task assigned to the incoming user 020 may be to check the blood pressure of the patient, to carry out a treatment plan for the low blood pressure, etc. For assigning the task, the reporting subsystem 160 may make use of predefined rules which associate information to be communicated with tasks. Such predefined rules may be provided by guidelines. Alternatively or additionally, the reporting subsystem 160 may make use of an interference engine to infer such a task.

As shown in FIG. 1, the system 100 may further comprise a presentation subsystem 180 for presenting the handover data 122 during the handover event. FIG. 1 shows the presentation subsystem 180 being connected to a display 080 in the room in order to present the handover data 122 to the outgoing user 010 and the incoming user 020. For that purpose, the presentation subsystem 180 is shown to provide presentation data 182 to the display 080. Moreover, the presentation subsystem 180 is shown to receive the handover data 122 via the monitoring subsystem 140. Alternatively, the presentation subsystem 180 may receive the handover data 122 directly from the interface 120. The presentation subsystem 180 may present the handover data 122 in various forms. For example, if the handover data 122 is constituted by a handover presentation or a handover task list, the presentation subsystem 180 may directly display the handover presentation or the handover task list on the display 080. Alternatively, the presentation subsystem 180 may convert the handover data 122 into a displayable format before displaying the handover data 122 on the display 080.

Figure 4:
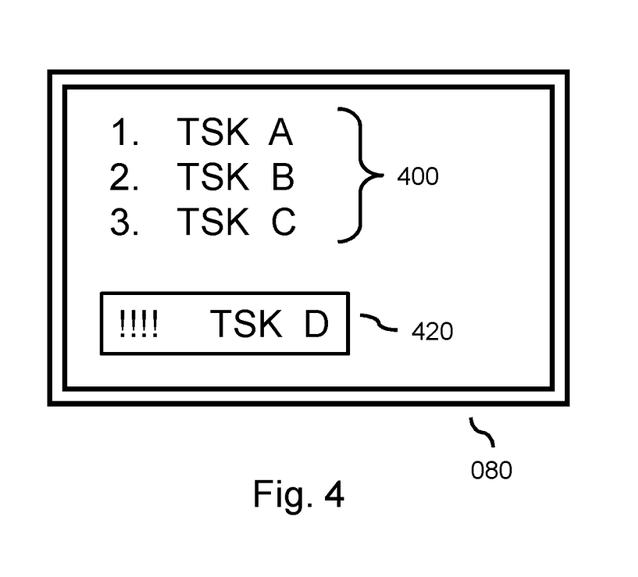
FIG. 4 shows handover data being presented on a display.

FIG. 4 shows an example of the handover data 122 being presented on the display 080. Here, the handover data 122 comprises a plurality of tasks labeled "TSK A", "TSK B", TSK C" 400 and "TSK D" 420 which indicates that information relating to these tasks is to be communicated from one or more outgoing users to one or more incoming users. In this example, the monitoring subsystem 140 is arranged for analyzing the sensor data 042 in real-time during the handover event and for providing feedback on a result of the analyzing, e.g., on the display 080. In particular, the reporting subsystem 160 may be arranged for issuing a warning if the information is deemed not to have been communicated at an end of the handover event. In the example of FIG. 4, the fourth task "TSK D" 420 is deemed not to have been communicated at the end of the handover event. Accordingly, the fourth task "TSK D" 420 is visually highlighted by exclamation marks and a bounding box so as to establish a warning. Here, the other tasks are deemed to have been communicated. Accordingly, no warning is provided for these tasks. It will appreciated that the warning may take various suitable forms, e.g., visual, auditory, etc. Moreover, said feedback may also be provided while the handover event is ongoing, in that tasks which relate to information which is deemed to have been communicated may already be marked as being handed over whereas tasks which relate to information which is deemed not to have been communicated yet are marked as being not yet handed over. As such, the fourth task "TSK D" 420 may be displayed distinctly from the other tasks to indicate that it is not handed over yet.

In general, the handover event may be a handover meeting scheduled for at least the outgoing user 010 and the incoming user 020, and the reporting subsystem 160 may be arranged for analyzing the handover data 122 to establish an agenda and/or a task list for the handover meeting. Establishing the agenda may involve estimating a time needed for communicating all of the information as indicated by the handover data. The presentation subsystem 180 may present the agenda and/or the task list during the handover meeting.

It is noted that the handover meeting scheduled for at least the outgoing user 010 and the incoming user 020 may be a physical meeting as well as a virtual meeting. In the latter case, telecommunication means such as video conferencing may be used to organize the handover meeting. It will be appreciated that in such a case, the sensor 040 may be constituted by a video camera which is primarily intended for the video conferencing. It may therefore not be needed to provide a separate sensor 040 for enabling the system 100 to obtain the sensor data 042. The handover event may also not involve the outgoing user 010 at all. Rather, the outgoing user 010 may have previously recorded the communication, and the handover event may be a time at which the recording of the communication is received or played back to the incoming user 020. For example, the outgoing user 010 may record an audio message in order to communicate the information to the incoming user 020. The handover event may be a time when the incoming user 020 listens to the audio message. The monitoring subsystem 140 may then determine whether the information was indeed received by the incoming user 020, i.e., whether the incoming user 020 was present during playback of the audio message, whether the incoming user 020 paid attention while listening, etc.

In general, the handover event may be a clinical handover event, the outgoing user 010 and the incoming user 020 may be clinical users, the information to be communicated may be clinical information, and the handover data 122 may be clinical handover data 122. It is noted, however, that the clinical context is not a limitation since the present invention equally applies in a non-clinical context, e.g., in an industrial context.

Figure 5:
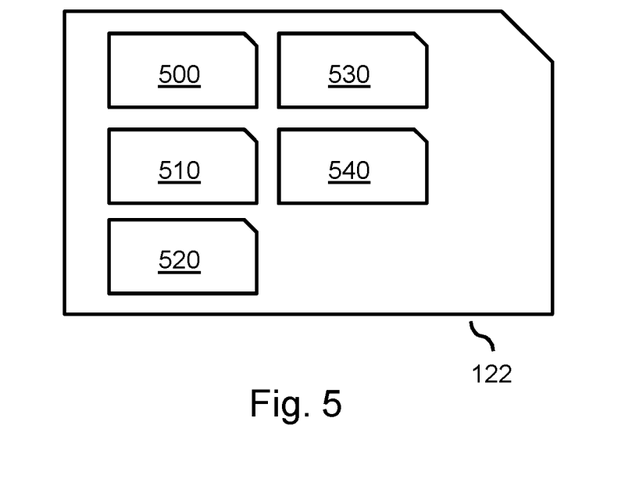
FIG. 5 shows a possible content of the handover data.

FIG. 5 shows a possible content of such clinical handover data 122. Here, the clinical handover data 122 is shown to be constituted by a note from one of the clinical users 500, an agenda of one of the clinical users 510, an electronic patient record 520, patient data from a patient monitor 530, and a clinical handover presentation 540. However, the handover data 122 may also have a different content. In particular, the handover data 122 may be primarily comprised of notes from clinical users of a current staff. The notes may reflect information which is to be communicated to a replacement staff. The interface 120 may be arranged for obtaining such clinical handover data 122 from a hospital information system.

It will be appreciated that the present invention may be advantageously used in the following clinical situation. During a current shift, a current staff may use electronic tools to keep track of the tasks which are to be completed or attended to during their shift. As their shift progresses, the current staff will typically achieve some tasks and realize that other task may need to be undertaken in the near future, e.g., during a next shift and consequently by a replacement staff. The electronic tool may enable tasks to be added via hand written or typed notes, speech, etc. Each note may consists of key pieces of information such as the what, who, why, where and when details, as prescribed by, e.g., NHS guidelines.

Each note may be sent by an electronic tool to a central database. In addition, the central database may include notes which were automatically generated, for example by patient monitors. The system may access such notes via the interface, thereby obtaining clinical handover data which is indicative of the information to be communicated during the clinical handover meeting between the current staff and the replacement staff. During the clinical handover meeting, the clinical handover data may be presented to the participants of said meeting. For example, the clinical handover data may be displayed on a large display such as a projection screen or a small display such as that of mobile devices. The clinical handover data may also be displayed on several displays simultaneously.

Video cameras such as those integrated into mobile devices may be used to obtain one or more video recordings of the participants during the clinical handover meeting. In case the clinical handover meeting is a virtual meeting, the video cameras and other sensors in the telecommunication devices of participants may be used for that purpose. The monitoring subsystem may then analyze the video recording(s) to determine whether participants have paid attention during the presentation of the clinical handover data. Additionally, participants may be asked to explicitly confirm that information has been handed over to them, e.g., by having to click a checkbox using the mobile device. The monitoring subsystem may also analyze the video recording or an audio recording to recognize the participants of the clinical handover meeting and to log their presence.

Additionally or alternatively, microphones such as those integrated into mobile devices may be used to obtain one or more audio recordings of the participants during the clinical handover meeting. The monitoring subsystem may then analyze the audio recording(s) using voice fingerprinting to recognize the participants of the clinical handover meeting and to log their presence. Also, the monitoring subsystem may analyze the audio recording(s) using speech recognition to obtain a transcript of the verbal communication, i.e., the discussion, between the participants. The transcript may be analyzed for keywords that correspond with the information as indicated by the clinical handover data. In case there is information indicated by the clinical handover data for which no discussion was detected during the clinical handover meeting, the monitoring subsystem may raise a warning.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for enabling, during a handover event, a secure handover of clinical patient information in a clinical environment between an outgoing clinical user and an incoming clinical user, the system comprising a handover space comprising an audio sensor, a video sensor, and a display, the system further comprising one or more processors and memory storing instructions, that, in response to execution by the one or more processors, cause the one or more processors to perform the following operations:

receiving handover data prior to the handover event, the handover data being indicative of clinical patient information to be communicated from the outgoing clinical user to the incoming clinical user during the handover event, wherein the handover data includes one or more items of patient data stored on a database;

determining, prior to the handover event and based on the handover data to be communicated, a plurality of keywords indicative of the handover data, wherein the plurality of keywords are utilized in determining if the handover data has been communicated from the outgoing clinical user to the incoming clinical user;

receiving sensor data from the audio sensor positioned within the handover space and monitoring the handover event in the clinical environment, comprising an audio recording from the handover event of communication between the outgoing clinical user and the incoming clinical user during the handover event;

receiving video data from the video sensor positioned within the handover space and monitoring the handover event in the clinical environment, comprising a video recording from the handover event of communication between the outgoing clinical user and the incoming clinical user during the handover event;

performing, using the one or more processors, speech recognition processing on the audio recording to generate speech recognition output and video recognition processing on the video recording to generate video recognition output;

analyzing, using the one or more processors, the speech recognition output in dependence on the plurality of keywords to determine whether the clinical patient information has been fully communicated to the incoming user during the handover event by searching the speech recognition output for each of the plurality of keywords and determining whether each of the plurality of keywords is present in the speech recognition output;

analyzing, using the one or more processors, the video recognition output to identify one or more non-verbal communications between the outgoing clinical user and the incoming clinical user;

identifying, using the one or more processors, at least a portion of the clinical patient information that was detected during the analyzing, wherein the clinical patient information is identified as detected when one or more of the plurality of keywords is determined to be present in the speech recognition output, and wherein the identified clinical patient information comprises communicated clinical patient information;

identifying, using the one or more processors, at least a portion of the clinical patient information that was not detected during the analyzing, wherein the clinical patient information is identified as not detected when one or more of the plurality of keywords is determined to not be present in the speech recognition output, and wherein the identified clinical patient information comprises clinical patient information that was not communicated;

identifying, using the one or more processors and the one or more non-verbal communications, at least a second portion of the clinical patient information that was not communicated, the identified second portion comprising non-verbal communication between the outgoing clinical user and the incoming clinical user; and reporting to the incoming clinical user, in the handover space via the display, a report of the handover event, comprising a visual indication of the communicated clinical patient information and the clinical patient information that was not communicated during the handover event;

wherein the clinical patient information that was not communicated during the handover event further comprises a visual warning on the display.

2. The system according to claim 1, further comprising instructions for analyzing the sensor data from the sensor monitoring the handover event in the clinical environment to determine a presence of the incoming clinical user during the handover event.

3. The system according to claim 2, wherein determining the presence of the incoming clinical user during the handover event further comprises applying a biometric identification technique to the sensor data to identify the incoming user.

4. The system according to claim 1, further comprising determining a level of attention of the incoming clinical user using the video recognition output.

5. The system according to claim 1, wherein the speech recognition output is analyzed in dependence on the one or more keywords in real-time during the handover event.

6. The system according to claim 1, further comprising instructions for providing output on the one or more computing devices indicative of the clinical patient information that was detected in addition to the clinical patient information that was not detected.

7. The system according to claim 1, wherein the handover event is a handover meeting scheduled for at least the outgoing user and the incoming user, and wherein determining, based on the handover data, one or more keywords indicative of the handover data further comprises:

determining, based on the handover data, at least one of an agenda and a task list, for the handover meeting.

8. A system according to claim 1, wherein the handover data is constituted by one or more of the group of: a note from one of the clinical users, an agenda of one of the clinical users, an electronic patient record, patient data from a patient monitor, and a clinical handover presentation.

9. The system according to claim 1, wherein the system further comprises a biometric identification system, and further comprising the steps of:

analyzing, using the biometric identification system, the audio recording and/or visual sensor data from the handover room; and determining, based on the analysis, the presence and/or identity of the outgoing clinical user and/or incoming clinical user.

10. The system according to claim 1, wherein the system further comprises a location identification system, and further comprising the steps of:

receiving location data from the incoming clinical user; and determining, by the location identification system, a presence and/or location of the incoming clinical user.

11. A method for enabling, during a handover event, a secure handover of clinical patient information in a clinical environment between an outgoing clinical user and an incoming clinical user, using a system comprising a handover space comprising an audio sensor, a video sensor, and a display, the system further comprising one or more processors, the method comprising:

accessing handover data prior to the handover event, the handover data being indicative of clinical patient information to be communicated from the outgoing clinical user to the incoming clinical user during auditory the handover event, wherein the handover data includes one or more items of patient data stored on a database;

determining, prior to the handover event and based on the handover data to be communicated, a plurality of keywords indicative of the handover data, wherein the plurality of keywords are utilized in determining if the handover data has been communicated from the outgoing clinical user to the incoming clinical user;

receiving sensor data from the audio sensor positioned within the handover space and monitoring the handover event in the clinical environment, comprising an audio recording from the handover event of communication between the outgoing clinical user and the incoming clinical user during the handover event;

receiving video data from the video sensor positioned within the handover space and monitoring the handover event in the clinical environment, comprising a video recording from the handover event of communication between the outgoing clinical user and the incoming clinical user during the handover event;

performing, using the one or more processors, speech recognition processing on the audio recording to generate speech recognition output and video recognition processing on the video recording to generate video recognition output;

analyzing, using the one or more processors, the speech recognition output in dependence on the plurality of keywords to determine whether the clinical patient information has been fully communicated to the incoming user during the handover event by searching the speech recognition output for each of the plurality of keywords and determining whether each of the one or more keywords is present in the speech recognition output;

analyzing, using the one or more processors, the video recognition output to identify one or more non-verbal communications between the outgoing clinical user and the incoming clinical user;

identifying, using the one or more processors, at least a portion of the clinical patient information that was detected during the analyzing, wherein the clinical patient information is identified as detected when one or more of the plurality of keywords is determined to be present in the speech recognition output, and wherein the identified clinical patient information comprises communicated clinical patient information;

identifying, using the one or more processors, at least a portion of the clinical patient information that was not detected during the analyzing, wherein the clinical patient information is identified as not detected when one or more of the plurality of keywords is determined to not be present in the speech recognition output, and wherein the identified clinical patient information comprises clinical patient information that was not communicated;

identifying, using the one or more processors and the one or more non-verbal communications, at least a second portion of the clinical patient information that was not communicated, the identified second portion comprising non-verbal communication between the outgoing clinical user and the incoming clinical user; and reporting to the incoming clinical user, in the handover space via the display, a report of the handover event, comprising a visual indication of the communicated clinical patient information and the clinical patient information that was not communicated during the handover event, wherein the clinical patient information that was not communicated during the handover event further comprises a visual warning on the display.

12. A non-transitory computer readable medium comprising instructions for causing a system comprising a handover space comprising an audio sensor, a video sensor, a display, and one or more processors to enable, during a handover event, a secure handover of clinical patient information in a clinical environment between an outgoing clinical user and an incoming clinical user by:

accessing handover data prior to the handover event, the handover data being indicative of clinical patient information to be communicated from the outgoing clinical user to the incoming clinical user during the handover event, wherein the handover data includes one or more items of patient data stored on a database;

determining, prior to the handover event and based on the handover data to be communicated, a plurality of keywords indicative of the handover data, wherein the plurality of keywords are utilized in determining if the handover data has been communicated from the outgoing clinical user to the incoming clinical user;

receiving sensor data from the audio sensor positioned within the handover space and monitoring the handover event in the clinical environment, wherein the sensor data includes an audio recording from the handover event of communication between the outgoing clinical user and the incoming clinical user during the handover event;

receiving video data from the video sensor positioned within the handover space and monitoring the handover event in the clinical environment, comprising a video recording from the handover event of communication between the outgoing clinical user and the incoming clinical user during the handover event;

performing speech recognition processing on the audio recording to generate speech recognition output, and performing video recognition processing on the video recording to generate video recognition output;

analyzing the speech recognition output in dependence on the plurality of keywords to determine whether the clinical patient information has been fully communicated to the incoming user during the handover event by searching the speech recognition output for each of the plurality of keywords and determining whether each of the plurality of keywords is present in the speech recognition output;

analyzing the video recognition output to identify one or more non-verbal communications between the outgoing clinical user and the incoming clinical user;

identifying, using the one or more processors, at least a portion of the clinical patient information that was detected during the analyzing, wherein the clinical patient information is identified as detected when one or more of the plurality of keywords is determined to be present in the speech recognition output, and wherein the identified clinical patient information comprises communicated clinical patient information;

identifying at least a portion of the clinical patient information that was not detected during the analyzing, wherein the clinical patient information is identified as not detected when one or more of the plurality of keywords is determined to not be present in the speech recognition output, and wherein the identified clinical patient information comprises clinical patient information that was not communicated;

identifying, using the one or more non-verbal communications, at least a second portion of the clinical patient information that was not communicated, the identified second portion comprising non-verbal communication between the outgoing clinical user and the incoming clinical user; and reporting to the incoming clinical user, in the handover space via the display, a report of the handover event, comprising a visual indication of the communicated clinical patient information and the clinical patient information that was not communicated during the handover event, wherein the clinical patient information that was not communicated during the handover event further comprises a visual warning on the display.

\* \* \* \* \*